United States Patent [19]

Ward

[11] Patent Number: 4,555,311

[45] Date of Patent: Nov. 26, 1985

[54] INTEGRATED FRACTIONATION IN THE RECOVERY OF ALKYLAROMATIC HYDROCARBONS

[75] Inventor: Dennis J. Ward, South Barrington, Ill.

[73] Assignee: UOP Inc., Des Plaines, Ill.

[21] Appl. No.: 553,343

[22] Filed: Nov. 18, 1983

[51] Int. Cl.[4] .............................. B01D 3/00; C07C 3/54
[52] U.S. Cl. ......................................... 203/21; 203/25; 203/71; 203/98; 203/99; 585/719
[58] Field of Search .................... 203/21, 25, 27, 71, 203/99, 98, 75, 78, 82, 84, DIG. 19; 585/719, 450, 451; 208/353

[56] References Cited

U.S. PATENT DOCUMENTS

| | | | |
|---|---|---|---|
| 3,254,024 | 5/1966 | Huckins, Jr. et al. | 208/354 |
| 3,367,846 | 2/1968 | Uitti et al. | 203/25 |
| 3,414,484 | 12/1968 | Carson et al. | 203/26 |
| 3,499,826 | 3/1970 | Sulzabch et al. | 203/27 |
| 3,518,165 | 6/1970 | Ward | 203/78 |
| 3,520,944 | 7/1970 | Ward | 585/451 |
| 3,639,497 | 2/1972 | Martel et al. | 203/25 |
| 3,763,022 | 10/1973 | Chapman | 203/25 |
| 4,051,191 | 9/1977 | Ward | 260/671 R |
| 4,128,597 | 12/1978 | Jones | 585/719 |
| 4,144,281 | 3/1979 | Chapman et al. | 585/719 |
| 4,170,548 | 10/1979 | Ruth | 208/351 |
| 4,182,924 | 1/1980 | Chapman | 585/719 |
| 4,225,741 | 9/1980 | Chapman et al. | 585/719 |
| 4,311,866 | 1/1982 | Chapman | 585/719 |

*Primary Examiner*—S. Leon Bashore
*Assistant Examiner*—Virginia Manoharan
*Attorney, Agent, or Firm*—Thomas K. McBride; William H. Page, II; John F. Spears, Jr.

[57] ABSTRACT

A method is disclosed for fractionating a hydrocarbon conversion zone effluent stream comprising at least three components which are to be isolated into separate streams. A two-column system for fractionating the effluent of a benzene alkylation zone is employed. The overhead vapor of a downstream second column is condensed in a side reboiler of a preceding recycle column. This side reboiler is located between the feed point to the recycle column and a separate reboiler located at the bottom of the recycle column. The utilities cost of performing the fractionation is reduced.

4 Claims, 1 Drawing Figure

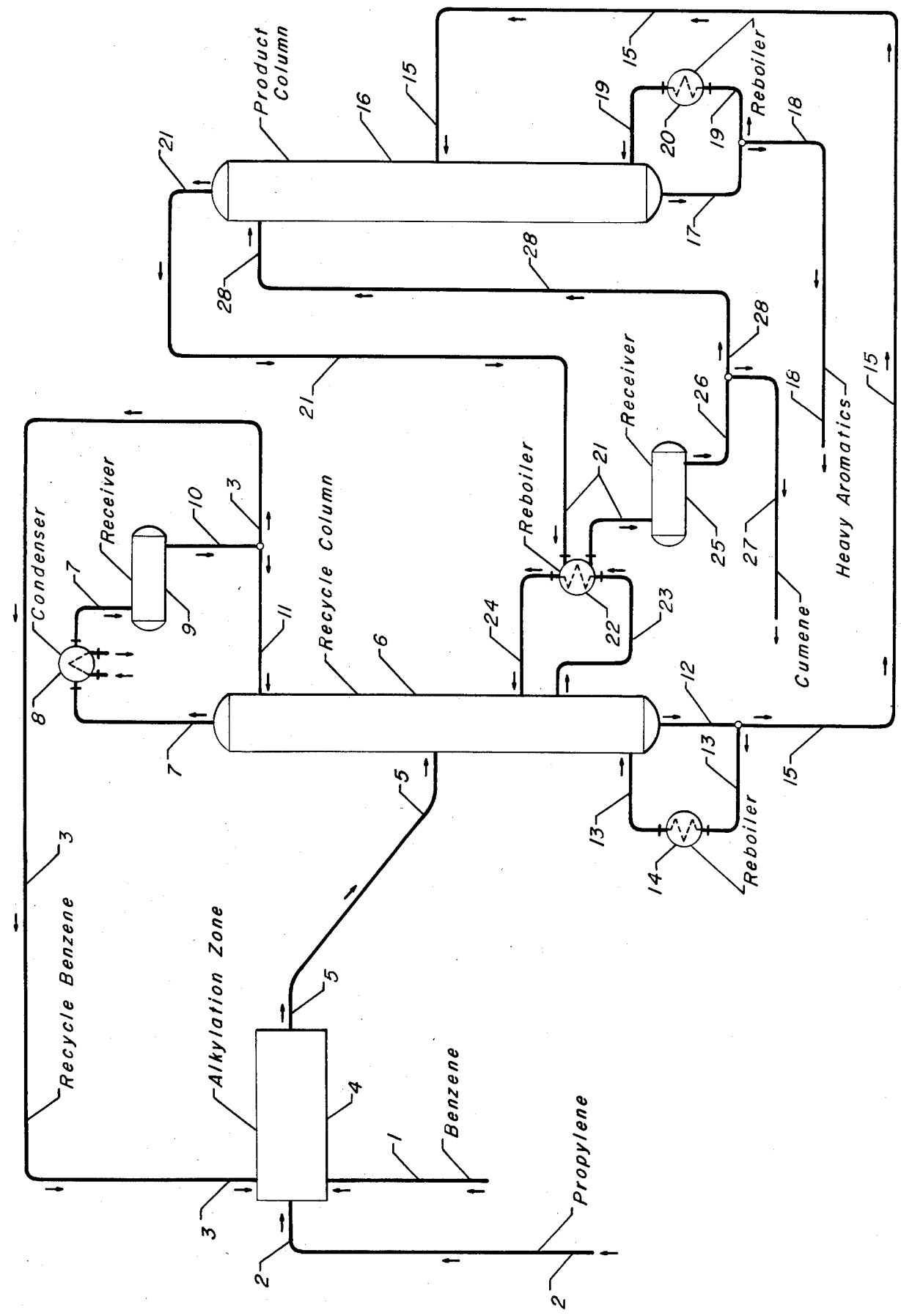

INTEGRATED FRACTIONATION IN THE RECOVERY OF ALKYLAROMATIC HYDROCARBONS

FIELD OF THE INVENTION

The invention in general relates to the processing of hydrocarbons and to the recovery of specific hydrocarbons from the effluent of a hydrocarbon conversion process. The invention is directly concerned with the recovery of a product alkylaromatic hydrocarbon from the effluent of an alkylation zone. The invention directly concerns the fractional distillation methods employed in the separation of an alkylaromatic hydrocarbon from an alkylation zone effluent stream.

PRIOR ART

The alkylation of aromatic hydrocarbons is a widely practiced commercial process. It may be performed for the production of an end product or an intermediate product which is the feedstock for a subsequent process or processing step. For instance, benzene may be reacted with a linear olefin for the production of linear alkylbenzenes suitable for conversion into soft detergent. The subject invention is, however, more directly concerned with the alkylation processes in which a feed aromatic hydrocarbon is reacted with another hydrocarbon having from two to about four carbon atoms per molecule. In this instance, the difference in the molecular weight and volatility between the feed aromatic hydrocarbon and the product alkylaromatic hydrocarbon is less than in the case of the production of detergent alkylate, since the normal olefin feedstock in a detergent alkylation process normally has from about 8 to about 15 carbon atoms per molecule. A typical alkylation process of the type believed most relevant to the subject invention is illustrated in U.S. Pat. No. 4,051,191. This patent provides a description of the operation of the alkylation zone and the fractionation system used to produce cumene by the alkylation of benzene with propylene. This reference illustrates the passage of a net liquid phase alkylation zone effluent stream into a first fractionation column labeled as the recycle column. Unreacted benzene is recovered as a net overhead product of the recycle column and returned to the alkylation zone. A bottoms product is removed from the recycle column and passed into a second fractionation column in which the product cumene is separated into a net overhead product. This two column arrangement is similar to that used in the subject invention.

It is well known to those skilled in the art that significant economies can be obtained in a fractionation process by utilizing the heat recovered from the overhead stream of a fractionation column within the fractionation process itself. The overhead vapor stream may therefore be cooled by indirect heat exchange against a fluid which requires heating or vaporization. An example of this is shown in U.S. Pat. No. 3,414,484 issued to D. B. Carson in which the overhead vapor stream of an aromatic fractionation column is compressed to thereby provide a stream having a sufficient temperature to reboil the column from which it is removed. This is normally referred to as a heat pumped fractionation system.

U.S. Pat. No. 3,254,024 issued to H. A. Huckins, Jr. illustrates a process for the separation of $C_8$ aromatic hydrocarbons by fractional distillation. This reference is believed pertinent for its illustration of the removal of the overhead vapor stream from the fractionator 7 and the passage of this overhead vapor through the bottom reboiler means employed in the fractionators 2 and 13. This demonstrates that it is known to those skilled in the art that the overhead vapor stream of one fractionation column may be utilized to reboil a different fractionation column through the proper selection of operational conditions. A similar but slightly different fractionation method is illustrated in U.S Pat. No. 4,170,548 issued to R. G. Ruth. In this reference, the overhead vapor stream of a column 12 is used as the heat source employed in the reboiler 16 of a second column. The overhead vapor stream is then condensed and collected in an overhead receiver. A first portion of the collected condensate is returned to the column 12 as reflux and a second portion is passed into the second column.

BRIEF SUMMARY OF THE INVENTION

The subject invention provides an improved process which reduces the utility cost of recovering a product alkylaromatic hydrocarbon from an admixture comprising both lower boiling and higher boiling aromatic hydrocarbons. The subject process utilizes energy available in the overhead stream of a second fractionation column in a side reboiler located between the feed tray and the bottom of a preceding fractionation column. This significantly reduces the amount of energy required in the reboiler located at the bottom of the first fractionation column. The subject process may be characterized as comprising the steps of passing the reaction zone effluent stream which comprises a $C_6$-plus aromatic first hydrocarbon, an aromatic second alkylaromatic hydrocarbon and a heavy by-product alkylaromatic third hydrocarbon into a first fractionation column at a first point, with the first fractionation column being maintained at fractionation conditions in part through the use of a first reboiler means located at the bottom of the first fractionation column; removing an overhead stream, which is rich in the first hydrocarbon, from the first fractionation column; removing a first net bottoms stream, which is rich in the alkylaromatic second hydrocarbon, from the first fractionation column and passing the first net bottoms stream into a second fractionation column; removing a second net bottoms stream, which is rich in the by-product alkylaromatic third hydrocarbon, from the second fractionation column; and condensing at least a portion of an overhead vapor stream which is withdrawn from the second fractionation column by indirect heat exchange as the heat source employed in a second reboiler means which vaporizes a portion of the liquid present within the first fractionation column at an intermediate lower second point, and recovering a product stream which is rich in the product alkylaromatic second hydrocarbon from the condensate which results from this heat exchange in the second reboiler means.

BRIEF DESCRIPTION OF THE DRAWING

The drawing is a simplified flow diagram of an alkylation process for producing cumene and which utilizes a preferred embodiment of the invention.

A feed stream of relatively high purity benzene carried by line 1 together with a propylene-containing feed stream carried by line 2 and the benzene-rich recycle stream of line 3 are passed into the alkylation zone 4. In this zone, these three streams are brought into contact with an alkylation catalyst at alkylation-promoting conditions which result in the reaction of a portion of the benzene with the available propylene. The material being withdrawn from the reaction zone is separated within the alkylation zone as required by the specific alkylation zone and propylene feed streams which are being employed. This may produce recycle streams and off-gas streams not shown and also produces an alkylation zone effluent stream removed in line 5. The alkylation zone effluent stream comprises an admixture of benzene, cumene, and various higher boiling by-product hydrocarbons produced by reactions other than the intended monoalkylation of the benzene.

The alkylation zone effluent stream is passed into a first fractionation column 6 referred to as a recycle column. Substantially all of the benzene and any lighter hydrocarbons is concentrated into a net overhead vapor stream removed through line 7 and passed through the overhead condenser 8. The resultant condensate is collected in the overhead receiver 9. Uncondensed gases which may be present and condensed water may be removed through means not shown. The hydrocarbon condensate is withdrawn from the overhead receiver through line 10 and divided into a first portion which is returned to the recycle column through line 11 as reflux and a second portion which is recycled to the alkylation zone as the benzene recycle stream carried by line 3. Substantially all of the hydrocarbons entering the fractionation column which are less volatile than benzene are concentrated into a bottoms liquid stream withdrawn from the recycle column in line 12. A first portion of the bottoms liquid is diverted through an external reboiler means 14 via line 13. The fluids discharged from the bottom reboiler 14 are passed into a bottom portion of the recycle column.

The remaining portion of the bottoms stream of line 12 becomes the feed stream charged to the product column 16 through line 15. The relatively small amount of high boiling by-products which enters the product column becomes concentrated into a bottoms stream withdrawn in line 17. This bottoms liquid is divided into a portion which is passed through a reboiler means 20 via line 19 and a second portion withdrawn as a by-products stream through line 18. The very great majority of the material which enters the product column 16 is concentrated into the overhead vapor stream removed from the products column in line 21. The overhead vapor stream passes through a side reboiler means 22 wherein it is condensed to form an overhead condensate which is passed into the overhead receiver 25. The condensate is withdrawn through line 26 and divided into a first portion returned to the products column via line 28 as reflux and a second portion which is withdrawn as the cumene product stream through line 27. The substantial amount of heat of vaporization given up by the overhead vapor stream of the products column is received by a liquid stream withdrawn from an intermediate point in the lower half of the recycle column in line 23. This liquid is preferably partially vaporized in the side reboiler 22 to thereby produce a mixed phase stream which is charged to the recycle column 6 through line 24. Line 24 communicates with the recycle column at a point which is at least several trays above the point at which vapors produced by the bottom reboiler means 14 enter the recycle column. This description of a preferred embodiment of the invention is not intended to preclude from the scope of the invention those other embodiments set out herein or which are the result of the normal and expected modification of those embodiments.

DETAILED DESCRIPTION

The alkylation of aromatic hydrocarbons is practiced commercially on a large scale. One particular example is the alkylation of benzene with propylene to form cumene, which is then used to produce phenol and acetone. These alkylation processes are normally performed with the intent of producing a single alkylaromatic product rather than an admixture of alkylaromatics. However, despite the advances in the art which have occurred, the products of the commercial alkylation reactor will normally contain an admixture which contains small amounts of byproducts which must be separated from the reaction zone product. Further, in an effort to promote monoalkylation, there is normally provided an excess of the feed aromatic hydrocarbon which is to be alkylated. The effluent of the alkylation reaction zone therefore normally contains an admixture of the feed hydrocarbon, the product hydrocarbon, and one or more higher boiling side products. The separation of these materials is normally performed commercially by fractional distillation.

The separation of these sometimes close-boiling hydrocarbons in large quantities and to high purities requires sizable fractionation facilities and consumes a large amount of energy. The utilities cost of the fractionation includes both the cost of heat supplied to the reboiler of the fractionation column and the cost in terms of cooling water and wasted low level heat which is associated with the condensation of overhead vapors. The utilities cost of separating the effluent stream of the alkylation zone is therefore a significant part of the total cost of operating such an aromatic hydrocarbon alkylation process. It is therefore an objective of the subject process to provide a method of reducing the utilities cost of operating the fractionation section of a process for the alkylation of aromatic hydrocarbons. It is another objective of the subject invention to provide a method of recovering in a useful manner heat present in the overhead vapor stream of the product column of a two-column aromatic hydrocarbon fractionation system. It is a specific objective of the subject invention to reduce the reboiler heating utilities cost of the recycle column of a process in which cumene is produced by the alkylation of benzene.

The subject process may be used to separate the effluent of reaction zones used for transalkylation, alkylaromatic hydrocarbon isomerization, aromatization, etc. However, the preferred reaction is alkylation and the process will be described mainly in terms of this one limited embodiment. The preferred feed hydrocarbon for alkylation is benzene. The preferred hydrocarbon feed material may be more generally characterized as an aromatic $C_6$-plus hydrocarbon such as benzene, toluene, a xylene, or ethylbenzene. Higher molecular weight hydrocarbons could also be consumed as the feed hydrocarbon. The alkylating agent which is reacted with the feed hydrocarbon to produce the product alkylaromatic hydrocarbon may be an olefin-acting compound such as an alcohol, ether or ester including alkylhalides, alkylsulfates and alkylphosphates. Preferably, the alkylating agent is a mono- or diolefin having from two to five carbon atoms per molecule. The preferred monoolefins include ethylene, propylene, butene-1, butene-2 and isobutylene. These olefins may be used as relatively pure streams containing a single hydrocarbon species.

Alternatively, a mixture of a single olefin and a corresponding paraffin may be used or a mixture of two or more olefinic hydrocarbons may be employed as the olefin-containing material charged to the alkylation zone. Typical product hydrocarbons include cumene, ethylbenzene, and cymene (isopropyltoluene).

The hydrocarbon stream charged to the fractionation zone is the effluent stream of a hydrocarbon conversion zone. This effluent stream is preferably the result of a partial separation performed within the conversion zone which results in a reaction zone effluent stream being converted into a conversion zone effluent stream containing less than 10 mol percent of any hydrocarbon having fewer carbon atoms per molecule than the hydrocarbon which is recovered as the overhead product of the first fractionation column. Preferably, this is achieved through a partial condensation of the admixture of compounds actually exiting from the reactor to produce a liquid hydrocarbon phase and a vapor phase containing a very great percentage of any hydrogen and normally gaseous hydrocarbons which exit the catalyst bed. The liquid phase produced in this manner may be stripped of dissolved light gases if desired prior to being passed into the fractionation zone of the subject invention. The subject improved separation method could be applied in general to the separation of an reaction zone effluent stream comprising an admixture of hydrocarbons having the appropriate boiling point characteristics including those processes described above. However, it is greatly preferred that the reaction zone is intended to operate as an alkylation zone in which the feed hydrocarbon is consumed in the production of a product hydrocarbon of higher molecular weight. This alkylation may be promoted through the use of a wide variety of suitable catalysts such as boron trifluoride, various zeolitic compounds, hydrogen fluoride, etc. The preferred catalyst for use in the alkylation zone is referred to as a solid phosphoric acid or SPA catalyst.

Suitable SPA catalysts are available commercially. As used herein the term "SPA catalyst" or its equivalent is intended to refer generically to a solid catalyst which contains as one of its principal raw ingredients an acid of phosphorus such as ortho-, pyro- or tetraphosphoric acid. These catalysts are normally formed by mixing the acid with a siliceous solid carrier to form a wet paste. This paste may be calcined and then crushed to yield catalyst particles, or the paste may be extruded or pelleted prior to calcining to produce more uniform catalyst particles. The carrier is preferably a naturally-occurring porous silica-containing material such as kieselguhr, kaolin, infusorial earth and diatomaceous earth. A minor amount of various additives such as mineral talc, fullers earth and iron compounds including iron oxide have been added to the carrier to increase its strength and hardness. The combination of the carrier and the additives normally comprises about 15-30 wt. % of the catalyst, with the remainder being the phosphoric acid. However, the amount of phosphoric acid used in the manufacture of the catalyst may vary from about 8-80 wt. % of the catalyst as described in U.S. Pat. No. 3,402,130. The amount of the additive may be equal to about 3-20 wt. % of the total carrier material. Further details as to the composition and production of typical SPA catalysts may be obtained from U.S. Pat. Nos. 3,050,472, 3,050,473 and 3,132,109 and from other references.

It is known in the art that the passage of aromatic hydrocarbons through an alkylation zone tends to leach chemically combined water out of an SPA catalyst. This is acknowledged in U.S. Pat. Nos. 3,510,534 and 3,520,945, the latter of which is directed to the control of the state of hydration of the catalyst. The water content of the catalyst is important since dehydration causes the SPA catalysts to deteriorate by powdering and caking, while excess water causes the catalysts to soften and eventually form a sludge which would plug the reactor. Water is therefore injected into the feed stream to maintain the catalyst at the proper state of hydration by replacing the water leached from the catalyst. The rate of this injection is used to control the catalyst hydration level, and the feed streams are therefore maintained as dry as practical prior to the water injection point. This results in the total water content of the feed being essentially the same as the amount injected. Typical water injection rates are from about 100 to 2000 ppm in aromatic hydrocarbon alkylation operations. A preferred water addition rate during the production of cumene is from about 200 to 300 ppm of the combined feed to the reaction zone.

The feed hydrocarbon, any recycle streams and the feed olefinacting compound are preferably admixed and then passed into a reaction zone. The reaction zone is maintained at alkylation-promoting conditions which include a pressure of about 300 to 1000 psig and a temperature of about 300° to 600° F. The liquid hourly space velocity of reactants may range from about 0.5 to 2.5. It is preferred that an excess of the aromatic hydrocarbon be present in the reaction zone. The mole ratio of the aromatic hydrocarbon to the olefin should be within the broad range of 3:1 to 20:1. A ratio of about 8:1 is preferred for the production of cumene. It is preferred that the reactant stream be mixed phase through the reactor. The feed stream therefore preferably contains some unreactive light paraffins having the same number of carbon atoms per molecule as the olefin. In the production of cumene it is preferred that the amount of propane in the reaction zone feed stream be at least equal to the amount of propylene in this stream. This may be accomplished by using a dilute propylene feed stream or by recycling propane.

In the preferred embodiment the effluent of the alkylation reactor is passed into a first rectifier column located within the complex referred to herein as the alkylation zone. This column is normally used in conjunction with either a second rectifier, an absorber or a depropanizer (for alkylation using propylene). The exact form of this system does not influence the subject process. The function of this portion of the alkylation zone is to recover any olefin-acting compound which may be available for recycling to the reactor and to remove any light hydrocarbons such as propane which enter the alkylation zone. The preferred form of this portion of the alkylation zone is described in previously referred to U.S. Pat. No. 4,051,191 and in U.S. Pat. No. 3,510,534.

The alkylation zone effluent will normally contain most of the excess benzene charged to the alkylation reactor to promote monoalkylation. It is common and preferred practice to first separate the feed benzene and other hydrocarbons boiling below the cumene (or other product) in a first fractionation column referred to as a benzene column or recycle column. The cumene or other product alkylaromatic is then recovered as the overhead of a second column referred to as the cumene column or product column. Further information on the preferred alkylation process and possible variations in process flows and operations may be obtained by reference to U.S. Pat. Nos. 3,437,706; 3,437,707; 3,437,708; 3,520,944 and 3,542,892.

The conditions of temperature and pressure maintained in the first and second fractionation columns are interrelated. They may, however, vary over considerable ranges, with exact operating conditions being set by economic and operational considerations which may be specific to individual process units. A broad range of conditions for use in the first fractionation column includes a top pressure of about 5 to about 150 psig and a bottoms temperature of about 270° to about 400° F. A broad range of conditions for use in the second fractionation column includes a top pressure of about 15 to about 240 psig and a bottoms temperature of about 320° to about 470° F. These conditions are interrelated in that the overhead vapor of the second column must be at a pressure such that it will be condensed at the temperature of the liquid in the side reboiler of the first column after adjustment for the temperature difference "across" the reboiler. The calculation of such fractionation conditions are well within the expertise of those skilled in hydrocarbon fractionation and may be aided by widely available computerized design systems. The internal design and construction of the columns may be similar to that presently employed in equivalent commercial installations.

The subject process requires a side reboiler to be installed in the first of the two columns. This reboiler is separate and distinct from the reboiler(s) employed at the bottom of the column. This reboiler is used to vaporize liquid withdrawn from an intermediate point in the column. As used herein, the term "intermediate point" is intended to indicate a point which is separated from each extremity of the colum by vapor-liquid contacting material equal to at least two and preferably three theoretical contacting stages (trays). The side reboiler therefore acts upon liquid which has a lower average boiling point than the bottoms liquid entering the bottom reboiler. The side reboiler preferably is located about midway between the bottom of the first column and the feed point to the column. However, the location of the feed point may be varied depending on the composition of the entering alkylation zone feed stream, and the feed may enter at such a level that the side reboiler is optimally placed much closer to the bottom reboiler than to the feed point.

The subject process recovers at least a major portion of the heat which must be removed in condensing the overhead stream of the second fractionation column. This heat is transferred into the first column. The amount of heat which must be applied to the customary bottom reboiler of the first column is thereby reduced and the utility cost of operating the column is lowered. For instance, the application of the subject process to a large scale process for the production of four hundred million pounds per year of cumeme is projected as being able to reduce the benzene (first) column reboiler heat requirements from about 33 million BTU/hr to about 18 million BTU/hr. This would provide a substantial reduction in the cost of operating the benzene column. Because the recovered heat is added to the benzene (first) column at a point above the bottom of the column, the required temperature of the cumene (second) column overhead vapor stream is lower than if it was attempted to use this overhead vapor as the heat source in the bottom reboiler. This assumes the pressure in the first column is the same during this comparison. The ability to recover heat from the overhead vapor at this lower temperature can be advantageous. For instance, the ability to apply modern heat recovery techniques to an existing pair of fractionation columns may be limited due to the maximum pressures at which the columns can be operated. An example of this would be the inability to operate an existing column at a sufficiently high pressure to achieve an overhead vapor having a temperature which can be used in reboiling at the bottom of another column. The subject process will allow heat in the overhead vapor to be used in the preceding column with a smaller pressure differential between the columns than the prior art method of consuming this heat at the bottom of the preceding column. The ability to recover heat from overhead vapors without a significant increase in the bottoms temperature of the second column may also be advantageous if the compounds being fractionated are thermally sensitive.

The subject process may be characterized as a process for recovering an alkylaromatic hydrocarbon from the effluent stream of an aromatic hydrocarbon alkylation zone which comprises the steps of passing an alkylation zone effluent stream which comprises a feed aromatic hydrocarbon, a product alkylaromatic hydrocarbon, and a by-product alkylaromatic having a higher boiling point than the product alkylaromatic hydrocarbon into a first fractionation column at a first intermediate point, with a first reboiler being located at the bottom of the first fractionation column; recovering a first net overhead product stream, which is rich in the feed hydrocarbon, from the first fractionation column; removing a first net bottoms stream, which is rich in the product alkylaromatic hydrocarbon, from the first fractionation column and passing the first net bottoms stream into a second fractionation column; removing a second net bottoms stream, which is rich in the by-product alkylaromatic hydrocarbon, from the second fractionation column; and condensing at least a portion of an overhead vapor stream withdrawn from the second fractionation column in a second reboiler by indirect heat exchange against liquid withdrawn from the first fractionation column at an intermediate second point located above the first reboiler and below said first intermediate point, and recovering a product stream which is rich in the product alkylaromatic hydrocarbon from the resultant condensate. As used herein, the term "rich" is intended to indicate that the stream or fluid being described contains over 60 mole percent of the specified compound or class of compounds. When the subject process is applied to conversion processes other than alkylation, the separations may be different from those described above. For instance, in aromatization processes in which aromatics are produced from $C_3$ and/or $C_4$ hydrocarbons, there will preferably be little or no "feed" hydrocarbon entering the first fractionation column. In this instance, benzene could be the top product of the first column, a mixture of toluene and xylenes may be removed as the top product of the second column and a mixture of $C_9$-plus aromatics withdrawn as the net bottoms product of the second column.

I claim as my invention:

1. A process for recovering an alkylaromatic hydrocarbon from the effluent stream of an aromatic hydrocarbon alkylation zone which comprises the steps of:
    (a) passing an alkylation zone effluent stream which comprises a feed aromatic hydrocarbon, a product alkylaromatic hydrocarbon, and a by-product alkylaromatic having a higher boiling point than the product alkylaromatic hydrocarbon into a first fractionation column at a first intermediate point, with a first reboiler being located at the bottom of the first fractionation column;

(b) supplying heat to the first fractionation column by vaporizing bottoms liquid by indirect heat exchange in said first reboiler and passing the resultant vapors into the first fractionation column, with the resultant vapor having a first temperature;

(c) recovering a first net overhead product stream, which is rich in the feed aromatic hydrocarbon, from the first fractionation column;

(d) removing a first net bottoms stream, which is rich in the product alkylaromatic hydrocarbon, from the first fractionation column and passing the first net bottoms stream into a second fractionation column;

(e) removing a second net bottoms stream, which is rich in the by-product alkylaromatic hydrocarbon, from the second fractionation column;

(f) supplying additional heat to the first fractionation column by vaporizing process liquid withdrawn at a second intermediate point located below said first intermediate point and having a lower average boiling point than the bottoms liquid entering the first reboiler in a second reboiler, with the created vapor having a second temperature lower than said first temperature;

(g) passing a second overhead vapor stream, which is withdrawn from the second fractionation column and is rich in said product alkylaromatic hydrocarbon, through the second reboiler in indirect heat exchange relationship with said process liquid withdrawn at said second intermediate point, which results in vaporizing said process liquid and at least partially condensing the second overhead vapor stream and thereby forming a condensate; and, (h) withdrawing a first portion of said condensate as a product steam of the process and passing a second portion of said condensate into the second fractionation column as reflux.

2. The process of claim 1 further characterized in that the feed aromatic hydrocarbon is toluene.

3. The process of claim 1 further characterized in that the feed aromatic hydrocarbon is benzene.

4. The process of claim 3 further characterized in that the product alkylaromatic hydrocarbon is cumene.

* * * * *